United States Patent [19]

Shibanuma et al.

[11] Patent Number: 5,710,353
[45] Date of Patent: Jan. 20, 1998

[54] PROCESS FOR FLUORINATING HALOGENATED HYDROCARBON

[75] Inventors: Takashi Shibanuma; Yasufu Yamada; Toshikazu Yoshimura; Hiroshi Momota, all of Settsu, Japan

[73] Assignee: Daikin Industries, Ltd., Osaka, Japan

[21] Appl. No.: 464,636

[22] PCT Filed: Dec. 9, 1993

[86] PCT No.: PCT/JP93/01787

§ 371 Date: Jun. 15, 1995

§ 102(e) Date: Jun. 15, 1995

[87] PCT Pub. No.: WO94/13610

PCT Pub. Date: Jun. 23, 1994

[30] Foreign Application Priority Data

Oct. 5, 1992 [JP] Japan ..................... 4-265877
Dec. 15, 1992 [JP] Japan ..................... 4-334174

[51] Int. Cl.$^6$ .......................... C07C 17/07; C07C 17/087
[52] U.S. Cl. .......................... 570/168; 570/166; 570/169
[58] Field of Search ........................... 570/168, 166, 570/169

[56] References Cited

U.S. PATENT DOCUMENTS

| 3,183,276 | 5/1965 | Vecchio | 570/168 |
| 3,413,360 | 11/1968 | Gardner | 570/168 |
| 3,442,962 | 5/1969 | Vecchio et al. | 570/169 |
| 5,171,901 | 12/1992 | Gassen et al. | 570/168 |

*Primary Examiner*—C. Warren Ivy
*Assistant Examiner*—Lyman H. Smith
*Attorney, Agent, or Firm*—Birch, Stewart Kolasch & Birch, LLP

[57] ABSTRACT

An object is to effectively preparing a fluorinated compound by developing a catalyst which is effective in the fluorination of a halogenated alkane or alkene with hydrogen fluoride by a gas phase fluorination or addition of hydrogen fluoride. To this end, a catalyst which comprises a least one element selected from the group consisting of Ti, V, Zr, Mo, Ge, Sn and Pb, and alumina, aluminum fluoride or partially fluorinated alumina is used. This catalyst is prepared by an impregnation method to support the above element on alumina and the like, or a precipitation method in which the catalyst is co-precipitated from a solution containing an aluminum compound and a compound of the above element.

11 Claims, No Drawings

PROCESS FOR FLUORINATING HALOGENATED HYDROCARBON

This application is a 35 USC 371 National Stage filing of PCT/JP93/01787 published as WO94/13610 on Jun. 23, 1994.

FIELD OF THE INVENTION

The present invention relates to a process for fluorinating a halogen-containing hydrocarbon. In particular, the present invention relates to a process for preparing a fluorine-containing compound by fluorinating a halogen-containing alkane or alkene with hydrogen fluoride.

BACKGROUND ART

The influence of fluoro- and chlorofluorocarbon gases on the global environment is a serious problem, and substitutes for them are required. As a molecular composition of the substitute fluorocarbon, it may be contemplated for a compound to have a molecular composition such that a chlorine atom or atoms of the chlorofluorocarbon is or are replaced with a fluorine atom or atoms. A candidate compound as a substitute fluorocarbon satisfying such condition has a larger fluorine content than the conventional compounds.

In a fluorination reaction to synthesize a molecule having a high fluorine content, the fluorination by a liquid phase reaction is not preferred, and the fluorination by a gas phase reaction is sought.

As a catalyst for the gas phase fluorination or an addition reaction of hydrogen fluoride, chromium oxide base and alumina base catalysts are known. As a catalyst for fluorination of a halogenated alkane or alkene, there is a chromium oxide catalyst (U.S. Pat. No. 3,258,500), an aluminum fluoride catalyst (U.S. Pat. No. 2,669,590), an alumina catalyst (GB Patent No. 1,357,246) or a partially fluorinated alumina catalyst (GB Patent No. 1,000,485).

Among them, the present invention relates to the alumina base catalyst. Alumina is widely known to be used as a carrier of a catalyst. In addition, a catalyst comprising activated alumina does not necessarily have a sufficient catalytic activity. Then, there have been developed modified catalysts such as a catalyst comprising a metal supported on alumina as a carrier (EP-A-0 331 991), a catalyst comprising a transition metal supported on basic aluminum fluoride or activated alumina (GB Patent No. 805,503 and WO 89/10341), and a ternary catalyst comprising aluminum (JP-A-60 6927). However, the sufficient activity is not necessarily achieved.

SUMMARY OF THE INVENTION

An object of the present invention is to provide a process for effectively preparing a fluorinated compound by developing a catalyst which is effective in the fluorination of a halogenated alkane or alkene with hydrogen fluoride by a gas phase fluorination or addition of hydrogen fluoride, respectively.

An aspect of the present invention resides in a process for fluorinating a halogenated hydrocarbon comprising fluorinating a halogenated alkane or alkene having 1 to 5 carbon atoms with hydrogen fluoride in a gas phase reaction or through addition of hydrogen fluoride, respectively, in the presence of a catalyst which comprises a least one element selected from the group consisting of Ti, V, Zr, Mo, Ge, Sn and Pb, and alumina, aluminum fluoride or partially fluorinated alumina.

The present invention will be explained in detail.

DETAILED DESCRIPTION OF THE INVENTION

Examples of the halogenated alkane to be used as a raw material in the present invention are $CH_2Cl_2$, $CH_2ClF$, $CF_3CCl_2H$, $CF_3CHClF$, $CF_3CH_2Cl$, $CF_2ClCFCl_2$, $CF_3CCl_3$, $CF_3CFCl_2$, $CF_2ClCF_2Cl$, $CCl_3CH_3$, $CH_3CFCl_2$, $CH_3CF_2Cl$, $CCl_4$, $CF_2HCF_2CH_2Cl$, and so on. Haloalkanes such as halobutane or halopentane may be used.

As the halogenated alkene, $CH_2=CHCl$, $CCl_2=CClH$, $CCl_2=CC_2$, $CF_2=CClH$, $CF_2=CFH$, $CCl_2=CClCCl=CCl_2$, and so on.

Among them, $CF_2=CClH$ (hereinafter referred to as "HCFC1122") is obtained as a by-product in the production of $CF_3CFH_2$ (hereinafter referred to as "HFC-134a") by the reaction of $CF_3CH_2Cl$ (hereinafter referred to as "HCFC-133a") with hydrogen fluoride. It is difficult to separate by-produced HCFC-1122 and the main product HFC-134a by distillation. When hydrogen fluoride is added to HCFC1122, HCFC-133a, which is a raw material of HFC-134a, is obtained. Since HCFC-133a can be separated from HFC-134a by distillation, the present invention may be applied to the removal of HCFC-1122 contained in HFC-134a. U.S. Pat. No. 4,158,675 discloses to carry out this reaction in the presence of a chromium oxide catalyst.

The catalyst to be used in the present invention comprises (a) at least one metal element selected from the group consisting of Ti, V, Zr, Mo, Ge, Sn and Pb, and (b) alumina, aluminum fluoride or partially fluorinated alumina.

The catalyst can be prepared by an impregnation method or co-precipitation method. While either method can achieve the objects of the present invention, the catalyst prepared by the co-precipitation method has a very high activity.

In the impregnation method, the catalyst is prepared by impregnating alumina or aluminum fluoride with a solution of a starting material which comprises the above metal element, and removing a solvent. Then, in the catalyst prepared by the impregnation method, the metal element is supported on alumina and the like, and present mainly on its surface.

As alumina to be used as a carrier, alumina X-ray diffraction peaks of which are identified as those of γ-alumina including η-alumina is preferred. In this case, alumina is active alumina which has a fluorination activity such that it can be used alone.

As alumina, any commercially available alumina may be used. Examples are KHA-24, NKH1-24 (both trademarks, manufactured by Sumitomo Chemical Co., Ltd.), Neobead GB (trademark, manufactured by Mizusawa Chemical Co., Ltd.), N612N, N612N8 (trademark, manufactured by Nikki Chemical Co., Ltd.), etc.

As the starting material of the element to be impregnated, salts with inorganic acids such as chlorides, nitrides or sulfates, salts with organic acids such as acetates or propionates, and oxides of the above metal elements, and further oxyacids of the above metal elements or their salts can be used.

A proportion of the metal element in relation to alumina or aluminum fluoride is from 0.005 to 10 mole %, preferably from 0.05 to 5 mole %. When it is less than 0.005 mole %, the improvement of the catalytic activity is not expected. When it exceeds 10 mole %, the activity tends to decrease.

In a specific preparation method, for example, dehydrated alumina or aluminum fluoride is dipped in an aqueous solution or an organic solvent solution containing the element in a determined amount, and impregnated alumina or aluminum fluoride is dried under reduced pressure using an evaporator while stirring and then heated in air to dry it.

The supporting method is not limited to the above method. Any conventional impregnation method can be used, for example, alumina or aluminum fluoride is dipped in the solution after treating it in vacuum, or impregnated alumina or aluminum fluoride is dried by filtration instead of the vacuum suction. In these methods, partially fluorinated alumina can be used in place of alumina.

In the co-precipitation method, a precipitant is added to a solution of an aluminum compound and a compound comprising the above metal element dissolved in a common solvent such as water to co-precipitate them, and a precipitated material is calcined to obtain the catalyst. In the catalyst prepared by the co-precipitation method, not only the metal element is present on particle surfaces, but also the metal element is present inside the particles in addition to the particle surface.

As a starting material of the metal to be co-precipitated, the same compound as the starting material used in the above impregnation can be used.

In the catalyst prepared by the co-precipitation method according to the present invention, an amount of the above metal element is from 0.005 to 50 mole %. When it is less than 0.005 mole %, the objects of the present invention are not achieved. When it exceeds 50 mole %, the activity tends to decrease.

In an example of the preparation of the catalyst by the co-precipitation method, to an aqueous solution in which a salt of aluminum and a salt of the above metal element are dissolved in a determined ratio, a precipitant such as $NH_4OH$ is added till pH reaches 8 to 9 to precipitate them in the form of hydroxides, the precipitate is thoroughly washed with water and dried, and the dried material is shaped and then calcined at a temperature of 400 to 600° C. for 2 to 4 hours.

Preferably, the catalyst prepared by the impregnation or co-precipitation method is fluorinated before use in the reaction.

For fluorination, the catalyst is preferably contacted with hydrogen fluoride at a temperature higher than a reaction temperature. But, unnecessarily high temperature will decrease the catalytic activity. In addition to the selection of the fluorination temperature, it is preferred to suppress the temperature increase due to the fluorination reaction by dilution of hydrogen fluoride with nitrogen and so on. In general, the fluorination temperature is from 200° to 400° C. The fluorination of the catalyst is preferably carried out till a fluorine content reaches 50 to 80 wt. % (based on AlF3). When the catalyst is used in a high reaction temperature, the catalyst is preferably fluorinated up to about 90 wt. %. In the impregnation method, the fluorination of alumina may be carried out before the impregnation.

The prepared catalyst can be used in the reaction of the haloalkane or haloakene with hydrogen fluoride.

In this reaction, as a material of a reactor, a material having good resistance to hydrogen fluoride such as Inconel or Hastelloy should be used.

The reaction temperature depends on the kind of reaction, and is generally from 150° to 450° C.

A ratio of hydrogen fluoride to the raw material is usually at least 1 (one), when a chemical equivalent is 1 (one). This ratio may be large, but the increase of this ratio is not preferable for the process.

In the case of the addition reaction of hydrogen fluoride to HCFC-1122, a reaction temperature is usually from about 150° to 300° C., preferably from 150° to 250° C. While the reaction proceeds quickly at a higher temperature, HCFC-1122 cannot be decreased sufficiently at an excessively high temperature. Then, the reaction temperature varies with an intended amount of HCFC-1122. To decrease HCFC-1122, a molar ratio of HF to HCFC-1122 is advantageously larger than 1 (one). 1,1,1-Trifluoro-2-chloroethane (HCFC-133a) synthesized by the reaction is separated from HFC-134a by rectification. Separated HCFC-133a is reused as a raw material for the preparation of HFC-134a.

EXAMPLES

The present invention will be illustrated by the examples, which do not limit the scope of the present invention in any way.

Example 1

In a solution of 0.0015 mole of titanium chloride in 30 ml of water, 0.3 mole of alumina (N612N manufactured by Nikki Chemical Co., Ltd.), which had been dehydrated in an air at 250° C. for 12 hours, was dipped. After 12 hours, it was dried under reduced pressure in a rotary evaporator at about 60° C. while stirring and then in the air at 120° C. for 12 hours to obtain alumina containing titanium. Then, this catalyst was heated in a nitrogen gas up to 250° C., and hydrogen fluoride diluted with nitrogen to a hydrogen fluoride concentration of 17% was flowed over the catalyst for one hour. After increasing the hydrogen fluoride concentration to 50%, the hydrogen fluoride/nitrogen mixture was flowed over the catalyst for another one hour. Thereafter, the temperature was raised up to 300° C. over 30 minutes, and the hydrogen/nitrogen mixture was flowed for further one hour. After these treatments, alumina was fluorinated to 65% based on $AlF_3$.

The fluorinated catalyst (10 g) was filled in a Hastelloy tube having a diameter of 15 mm. Through the tube, a mixed gas of HF at 500 Nml/min., HFC-134a ($CF_3CFH_2$) at 85 Nml/min. and HCFC1122 ($CF_2=CHCl$) at 15 Nml/min. was flowed.

A conversion of HCFC-1122 ($CF_2=CHCl$) to HCFC-133a ($CF_3CH_2Cl$) was 36.6% at 175° C. A selectivity was 100 %.

In Examples 2-11 and Comparative Examples 1-5, the selectivity was 100%.

Example 2

In the same manner as in Example 1 except that 0.0015 mole of germanium oxide was used as the added element, a catalyst was produced and fluorinated. Then, the reaction was carried out under the same condition as in Example 1 using this catalyst. The conversion of HCFC-1122 to HCFC-133a was 38.5% at 175° C.

Example 3

In the same manner as in Example 1 except that 0.0015 mole of stannous chloride as an added element was dissolved in 30 ml of water (acidified with hydrochloric acid), a catalyst was produced and fluorinated. Then, the reaction was carried out under the same condition as in Example 1 using this catalyst. The conversion of HCFC-1122 to HCFC-133a was 35.5% at 175° C.

Example 4

In the same manner as in Example 1 except that 0.3 mole of alumina as used in Example 1 was dipped in a solution of 0.0027 mole of stannic chloride as an added element dissolved in 28 ml of ethanol, and the solvent was removed at 40° C. under reduced pressure, a catalyst was produced and fluorinated. Then, the reaction was carried out under the same condition as in Example 1 using this catalyst. The conversion of HCFC-1122 to HCFC-133a was 46.6% at 175° C.

Example 5

In the same manner as in Example 1 except that 0.00021 mole of ammonium paramolybdate as an added element was dissolved in 30 ml of water, a catalyst was produced and fluorinated. Then, the reaction was carried out under the same condition as in Example 1 using this catalyst. The conversion of HCFC-1122 to HCFC-133a was 38% at 175° C.

Example 6

In the same manner as in Example 1 except that 0.00043 mole of ammonium paramolybdate as an added element was dissolved in 30 ml of water, a catalyst was produced and fluorinated. Then, the reaction was carried out under the same condition as in Example 1 using this catalyst. The conversion of HCFC-1122 to HCFC-133a was 41.3% at 175° C.

Example 7

In the same manner as in Example 1 except that 0.0015 mole of ammonium metavanadate as an added element was dissolved in 30 ml of water, a catalyst was produced and fluorinated. Then, the reaction was carried out under the same condition as in Example 1 using this catalyst. The conversion of HCFC-1122 to HCFC-133a was 40.8% at 175° C.

Example 8

In the same manner as in Example 1 except that 0.0015 mole of lead nitrate as an added element was dissolved in 30 ml of water, a catalyst was produced and fluorinated. Then, the reaction was carried out under the same condition as in Example 1 using this catalyst. The conversion of HCFC-1122 to HCFC-133a was 35% at 175° C.

Example 9

In the same manner as in Example 1 except that 0.0015 mole of zirconium nitrate as an added element was dissolved in 30 ml of water, a catalyst was produced and fluorinated. Then, the reaction was carried out under the same condition as in Example 1 using this catalyst. The conversion of HCFC-1122 to HCFC-133a was 33% at 175° C.

Comparative Example 1

The same alumina as that used in Examples 1–10 was dehydrated at 250° C., and fluorinated in the same manner as in Example 1 without adding any metal element to obtain a catalyst. In the same manner as in Example 1 except that 10 g of this catalyst was used, the reaction was carried out. The conversion of HCFC1122 to HCFC-133a was 17.0% at 175° C.

Comparative Examples 2–4

In the same manner as in Example 1 except that 0.0015 mole of copper chloride, nickel chloride or silver nitrate was used as an added element, a catalyst was produced and fluorinated. Then, the reaction was carried out under the same condition as in Example 1 using each catalyst. The conversion of HCFC-1122 to HCFC-133a was 24%, 26.4% or 20.5%, respectively at 175° C. These catalyst had the lower activity than the catalyst composition of the present invention (with the same supported mole).

Example 10

With a 10% aqueous solution of aluminum nitrate (2 kg), a 30% aqueous solution of titanium sulfate was mixed so that a ratio of Ti/Al was 5 mole %. To the stirred mixture, 4N aqueous ammonia was added till pH reached 8.58, and a precipitated material was separated by centrifugal separation. After twice repeating washing with pure water and centrifugal separation, a resulting cake was dried at 120° C. for 14 hours. Then, the dried cake was ground and size adjusted, shaped by tabletting and calcined at 500° C. for 3 hours.

This catalyst was fluorinated in the same manner as in Example 1, and 10 g of the fluorinated catalyst was filled in a Hastelloy tube having an inner diameter of 15 mm. Then, HCFC-1122 and hydrogen fluoride was reacted under the same condition as in Example 1. The conversion of HCFC-1122 to HCFC-133a was 98.4% at 175° C.

Comparative Example 5

A catalyst consisting of alumina alone was produced by the same method as the method of Example 10 for producing the alumina/titanium oxide catalyst except that titanium sulfate was not mixed. From the X-ray diffraction peaks, this alumina was identified as γ-alumina containing η-alumina.

This alumina was fluorinated in the same manner as in Example 1.

Then, the reaction was carried out under the same condition as in Example 1 using each catalyst. The conversion of HCFC-1122 to HCFC-133a was 15% at 175° C.

Example 11

In the Hastelloy tube having an inner diameter of 15 mm, the same catalyst as that used in Example 10 (4 g) was filled. Through the tube, a mixed gas of HCC-30 ($CH_2Cl_2$) at 60 ml/min. and hydrogen fluoride at 200 ml/min. was flowed and reacted at 300° C. The conversion of HCC-30 was 75.7%, and the selectivity of HFC-32 ($CH_2F_2$) was 82%.

Example 12

In the Hastelloy tube having an inner diameter of 15 mm, the same catalyst as that used in Example 6 (4 g) was filled. Through the tube, a mixed gas of HCC-30 ($CH_2Cl_2$) and hydrogen fluoride was flowed and reacted under the same condition as in Example 11. The conversion of HCC-30 was 44.8%, and the selectivity of HFC-32 was 72.5%.

Example 13

In the Hastelloy tube having an inner diameter of 15 mm, the same catalyst as that used in Example 3 (4 g) was filled. Through the tube, a mixed gas of HCC-30 ($CH_2Cl_2$) and hydrogen fluoride was flowed and reacted under the same condition as in Example 11. The conversion of HCC-30 was 35%, and the selectivity of HFC-32 was 65%.

Comparative Example 6

In the Hastelloy tube having an inner diameter of 15 mm, the same catalyst as that used in Comparative Example 1 (4 g) was filled, and the reaction was carried out under the same condition as in Example 11. The conversion of HCC-30 was 16.4%, and the selectivity of HFC-32 was 46.3%.

Example 14

In the Hastelloy tube having an inner diameter of 15 mm, the same catalyst as that used in Example 6 (10 g) was filled. Through the tube, a mixed gas of perchloroethylene ($C_2Cl_4$) at 18 ml/min. and hydrogen fluoride at 181 ml/min. was flowed and reacted at 330° C. The conversion of perchloroethylene was 15.8%, and the selectivities of HCFC-123 ($CF_3CHCl_2$), CFC-1111 ($CCl_2=CClF$) and HCFC-122 ($CF_2ClCHCl_2$) were 94.7%, 3.4% and 1.6%, respectively.

Comparative Example 7

In the same manner as in Example 14 except that the same catalyst as that used in Comparative Example 1 (10 g) was used, the reaction was tried but the reaction of perchloroethylene did not proceed.

According to the present invention, the gas phase fluorination of the halogenated alkane with hydrogen fluoride and the addition of hydrogen fluoride to the halogenated alkene in the gas phase are effectively performed.

What is claimed is:

1. A process for producing a fluorinated saturated hydrocarbon comprising fluorinating a halogenated alkane or alkene having 1 to 5 carbon atoms with hydrogen fluoride in a gas phase reaction or through addition of hydrogen fluoride, respectively, in the presence of a catalyst which comprises:

(a) at least one element selected from the group consisting of Ti, V, Zr, Mo, Ge, Sn and Pb, and (b) alumina, aluminum fluoride or partially fluorinated alumina.

2. The process according to claim 1, wherein said halogenated alkane is $CH_2Cl_2$, $CH_2ClF$, $CF_3CCl_2H$, $CF_3CHClF$, or $CF_3CH_2Cl$.

3. The process according to claim 1, wherein said halogenated alkene is $CH_2=CHCl$, $CCl_2=CClH$, $CF_2=CClH$, or $CCl_2=CCl_2$.

4. The process according to claim 1, wherein said halogenated alkene is $CF_2=CClH$, and a reaction temperature is from 150° to 300° C.

5. The process according to claim 1, wherein said catalyst comprises:

(a) at least one element selected from the group consisting of Ti, V, Zr, Mo, Ge, Sn and Pb, and (b) alumina, wherein said alumina is prepared by a co-precipitation method.

6. The process according to claim 5, wherein said catalyst is fluorinated before it is used in the reaction.

7. The process according to claim 1, wherein said catalyst comprises:

(a) at least one element selected from Ti, V, Zr, Mo, Ge, Sn and Pb, and (b) alumina, aluminum fluoride or partially fluorinated alumina, wherein said alumina, aluminum fluoride or partially fluorinated alumina are prepared by an impregnation method.

8. The process according to claim 1 wherein said catalyst is fluorinated before it is used in the reaction.

9. The process according to claim 1, wherein said process is conducted at a reaction temperature of 150° to 450° C.

10. The process according to claim 1, wherein the fluorinated saturated hydrocarbon produced by said process contains an increased number of fluorine atoms and a reduced number of halogen atoms other than fluorine atoms.

11. The process according to claim 1, wherein said catalyst comprises:

(a) one element selected from the group consisting of Zr, V and Mo; and (b) alumina, aluminum fluoride or partially fluorinated alumina.

* * * * *